United States Patent [19]

Sepe

[11] Patent Number: 5,419,209
[45] Date of Patent: May 30, 1995

[54] SYSTEM AND PROTOCOL FOR RESIDENTIAL ENVIRONMENTAL ASSESSMENT

[75] Inventor: Louis J. Sepe, Moorestown, N.J.

[73] Assignee: Environmental Realty Guild of America, Inc., Philadelphia, Pa.

[21] Appl. No.: 31,792

[22] Filed: Mar. 15, 1993

[51] Int. Cl.$^6$ .............................................. G01N 1/00
[52] U.S. Cl. ................................................... 73/863
[58] Field of Search ........... 73/863.21, 863.23, 864.41, 73/864.43, 864.44, 864.71, 864.91, 863

[56] References Cited

U.S. PATENT DOCUMENTS

| | | | |
|---|---|---|---|
| 3,320,810 | 5/1967 | Stamulis et al. | 73/864.41 |
| 4,573,354 | 3/1986 | Voorhees et al. | 73/863.21 |
| 4,745,801 | 5/1988 | Luzier | 73/863.24 |
| 4,786,472 | 11/1988 | McConnell et al. | 73/863.21 |
| 4,801,800 | 1/1989 | Scheible | 73/863.21 |
| 4,805,468 | 2/1989 | Choudhey | 73/864.71 |
| 4,848,107 | 7/1989 | Gordon et al. | 73/864.71 |
| 4,991,452 | 2/1991 | Dillard et al. | 73/864.44 |
| 5,005,433 | 4/1991 | Patton | 73/864.44 |
| 5,047,207 | 9/1991 | Lankow et al. | 73/864.41 |
| 5,235,863 | 8/1993 | Bailey et al. | 73/863.21 |

Primary Examiner—Robert Raevis
Attorney, Agent, or Firm—Caesar, Rivise, Bernstein, Cohen & Pokotilow, Ltd.

[57] ABSTRACT

A system and protocol for the environmental assessment of residential properties and the like. The system includes a standard tool kit and standard equipment to be used by the inspector in inspecting and sampling suspected contaminants in the property. The inspector follows a precise protocol (step-by-step procedure) and also uses especially designed forms to record the inspection, the location of the suspected areas of contaminants, the type and number of samples of suspected contaminants taken, the readings taken of contaminant levels and the time at which the sampling and readings were taken. In addition, a specific checklist and reporting form is used to record the results of the inspection of the exterior of the building for the presence of suspected contaminants.

28 Claims, 12 Drawing Sheets

FIG. 3A  PHASE ZERO INSPECTION CHECKLIST

PROPERTY _____ DATE _____
_____ TIME _____
OWNER'S NAME _____ AGE OF PROPERTY _____
OWNER'S PHONE _____ WORK PHONE _____
OWNER'S ADDRESS _____

ASBESTOS
WHERE ANY OF THE FOLLOWING MATERIALS FOUND?
IN WHAT CONDITION? (F = FRIABLE, N = NONFRIABLE)
_ PIPE         _ BOILER        _ CEILING   _ DUCT          _ FLUE
  INSULATION    INSULATION      TILE         INSULATION     PACKING
_ FLOOR        _ PLASTER       _ LINOLEUM  _ OTHER _____
  TILE (9", 12") WALLS
WHAT ARE THE ACMs FOUND? _____
_____

CORRECTIVE ACTION? _____

RADON
SAMPLE # / LOCATION                      / START TIME / STOP TIME
_____ / _____ / _____ / _____
_____ / _____ / _____ / _____
COMMENTS: _____

PARTICULATES IN AIR
START TIME: _____ STOP TIME: _____ FLOW RATE: _____
LOCATION: _____ SAMPLE VOLUME: _____
COMMENTS: _____

VOLATILE ORGANIC COMPOUNDS
START TIME: _____ STOP TIME: _____ FLOW RATE: _____
LOCATION: _____ SAMPLE VOLUME: _____
COMMENTS: _____

UREA FORMALDEHYDE GAS
WAS ANY FOAM INSULATION PRESENT?     ___ YES  ___ NO
HAVE NEW COUNTERS, CABINETS, CARPETING, FURNITURE OR
DRAPES BEEN RECENTLY INSTALLED?      ___ YES  ___ NO
(CIRCLE THOSE PRESENT)
HAS FORMALDEHYDE GAS BEEN FOUND      ___ YES  ___ NO
BY DETECTOR TUBE?  HOW MUCH? _____ ppm  WHERE? _____
LIST LOCATIONS SAMPLED:  1) _____
                         2) _____

FIG. 3B

<u>LEAD-BASED PAINT</u>
ARE ANY PAINTED SURFACES PEELING OR CHIPPED? ____ YES ____ NO
WHERE AND HOW MUCH
(1-LOCALIZED, 2-LESS THAN 25% DAMAGE, 3-MORE THAN 25% DAMAGE)?
_____
_____

WIPE SAMPLES COLLECTED ____ YES ____ NO WHERE? _____
_____

BULK SAMPLES COLLECTED ____ YES ____ NO WHERE? _____
_____

<u>MUNICIPAL DRINKING WATER</u>
MUNICIPALITY'S COMPUTER ANALYSIS OBTAINED ON _____
SAMPLE OF DRINKING WATER TAKEN FROM _____

<u>VISUAL INSPECTION: INTERIOR</u>
ARE ANY FUEL TANKS PRESENT? ____ YES ____ NO
IF SO, WHERE? _____
ARE THEY PITTED? ____ YES ____ NO
ARE ANY CHEMICALS STORED ON-SITE?
IF SO, WHAT, WHERE, AND HOW MUCH? _____
_____
_____

ARE THERE ANY STAINS, SPILLS OR FLOOR DISCOLORATIONS WITHIN THE
BUILDING? IF SO, WHERE AND WHAT IS THE SUSPECTED CAUSE? _____
_____
_____

<u>VISUAL INSPECTION: EXTERIOR</u>
ARE ANY SURFACE WATERS PRESENT? ____ YES ____ NO
ARE SIGNS OF PETROLEUM PRESENT (SHEEN) ____ YES ____ NO
IS DEAD VEGETATION PRESENT? ____ YES ____ NO WHERE? _____
ARE VENT/FILL PIPES VISIBLE FOR UST'S ____ YES ____ NO HOW MANY? _____

DESCRIBE WEATHER CONDITIONS THE DAY OF INSPECTION.
BAROMETRIC PRESSURE IS _____
_____
_____

INSPECTION COMPANY _____

INSPECTOR'S NAME                    INSPECTOR'S SIGNATURE
_____                  _____
   (please print)

FIG. 3C

PROPERTY ADDRESS: _____
_____
_____

PROPERTY OWNER: _____

TEL NO'S: _____

TYPE OF BUILDING: _____

YEAR COMPLETED: _____

PROPERTY IS  _____ OCCUPIED _____ VACANT

PROPERTY DESCRIPTION: _____

PROPERTY USE: _____

INSPECTOR'S NAME: _____

DATE OF INSPECTION: _____

GENERAL REMARK(S):
PROPERTY/ADJACENT PROPERTY
_____
_____
_____

FIG. 3D

| ITEM | YES | NO | ASSUMED SUSPECT | UNK | REMARKS |
|---|---|---|---|---|---|

RADON

RADON SUSPECT ON
PROPERTY OR
NEIGHBORING PROPERTY
RADON SCREENING/TESTING
PREVIOUSLY CONDUCTED:

WASTE SITES: (TREATMENT,
STORAGE, OR TRANSPOR-
TATION, GENERATION OF
CHEMICALS OR HAZARDOUS
SUBSTANCES)
ON PROPERTY
NEIGHBORING PROPERTY:

STORAGE TANKS (VISIBLE):

UNDERGROUND STORAGE
TANKS (UST'S)
VENT/FILL PIPES (VISIBLE)

SOIL OR GROUND WATER
CONTAMINATION:

NEIGHBORING PROPERTY
   GAS STATION(S):
   MANUFACTURING PLANT(S):
   STORAGE/DELIVERY (OIL/GAS):
   FACILITIES: (OTHER)

ABOVE GROUND STORAGE
TANKS (AST'S)
SPECIFIC TANKS:

PROPERTY OWNER: _____
PROPERTY ADDRESS: _____
INSPECTORS NAME: _____
DATE OF INSPECTION: _____

COMMENTS: _____
_____
_____
_____

FIG. 4A

| TOXIC HAZ./MTL. | SAMPLED/ COLLECTED | TEST |
|---|---|---|
| RADON | ONE | CANNISTER (ON-SITE) LAB TEST (ONE) |
| VOC'S | ONE | AIR PUMP (ON-SITE) LAB TEST (ONE) |
| PARTICULATES | ONE | AIR PUMP (ON-SITE) LAB TEST (ONE) |
| UFFI | ONE OR MORE AS REQUIRED | DRAEGER DETECTION TUBE (ON-SITE) DIRECT READING |
| ASBESTOS | THREE TO FIVE | BULK SAMPLES (ON-SITE) LAB TEST (TWO) |
| LEAD IN WATER | ONE | STERILE JAR (ON-SITE) LAB TEXT (ONE) |
| LEAD BASED PAINT (OPT.) | TWO | BULK SAMPLES (ON-SITE) AND USE OF TEST SWABS. LAB TEST (TWO) OR USE OF (ON-SITE) XRF SPECTRUM ANALYZER (SCITEC) |

FIG. 4B(1)

| TOXIC & HAZARDOUS MATERIALS | SOURCE(S) | SAMPLING & TESTING | PROBABLE LOCATION ROOM/SPACE | REMEDIATION |
|---|---|---|---|---|
| A) RADON | HOMES BUILT ON RADON CONTAINING MATERIAL | PLACING CHARCOAL CANNISTER ON-SITE LAB TESTING | BASEMENT AREA OR LOWEST LIVABLE LEVEL | FILTER AIR INCREASE AIR VENTILATION |
| B) VOLATILE ORGANIC CHEMICALS (VOC's) | HOUSEHOLD FURNISHINGS CARPETS, DRAPERIES, FURNITURE | AIR SAMPLING (AIR PUMP) LAB TESTING | BASEMENT STORAGE AREAS LIVING/DINING RMS. (WALL COVERINGS) & FLOOR COVERINGS | FILTER AIR INCREASE AIR VENTILATION REMOVAL |
| C) PARTICULATES | TOBACCO SMOKE FIREPLACES, HOUSEHOLD CLEANING PRODUCTS | AIR SAMPLING (AIR PUMP) LAB TESTING | BASEMENT – ROOM WITH FIREPLACES OR ROOM WITH ROUGH FINISHED SURFACES (BRICK, STONE, WOOD) | FILTER AIR INCREASE AIR VENTILATION REMOVAL |

FIG. 4B(2)

| | | | |
|---|---|---|---|
| D) FORMALDEHYDE (UFFI) | USED AS BONDING RESIN IN CONSUMER PRODUCTS INCLUDING FURNITURE | DRAEGER DETECTION TUBE ON-SITE DIRECT READING | FOAM - ATTIC OR IN WALLS KITCHEN SHELVING CABINETS LIVING/DEN - PANELING | ABATEMENT - REMOVAL OF SOURCE OR ENCAPSULATION OR ENCLOSURE AIR VENTILATION |
| E) ASBESTOS | INSULATION & FIREPROOF MTL. SURFACE & THERMAL INSULATION MISCELLANEOUS | BULK SAMPLES LAB TESTING | ALL ROOMS | ABATEMENT - REMOVAL OF SOURCE ENCAPSULATION ENCLOSURE REPAIR |
| F) LEAD IN DRINKING WATER | LEAD PIPES & SOLDER JOINTS IN PIPES | ON-SITE COLLECTION STERILE JAR LAB TESTING | LARGEST CONSUMPTION OF WATER - KITCHEN OR SOURCE LOCATED AWAY FROM INCOMING WATER SOURCE | FILTER WATER REMOVAL OF LEAD PIPES OR LEAD SOLDER |
| G) LEAD BASED PAINT (OPTIONAL) | HOMES PRIOR TO 1978 LEAD PAINT | BULK SAMPLES LAB TEST OR XRF SPECTRUM ANALYZER | ALL ROOMS | ABATEMENT REMOVAL OF SOURCE OR ENCAPSULATION |

FIG. 4C

ITEMS (GENERAL)

| Item | A | B | C | D | E | F | G |
|---|---|---|---|---|---|---|---|
| ZIPLOCKING BAGS (SMALL & LARGE) |  | X | X | X | X |  | X |
| FLASH LIGHT | X | X | X | X | X | X | X |
| PLASTIC DROP CLOTH (4 MIL, 4'X 6') |  |  |  |  | X |  | X |
| CORE BORER |  |  |  |  | X |  |  |
| RAZOR KNIFE/PUTTY KNIVES |  |  |  |  |  |  | X |
| SILICONE ADHESIVE (TUBE) |  |  |  |  | X |  | X |
| SPRAY SEALANT |  |  |  |  | X |  | X |
| SPRAY CONTAINER (AMENDED WATER) |  |  |  |  | X |  |  |
| DUCT TAPE (GENERAL) | X | X | X | X | X |  | X |
| PAPER TOWELS (GENERAL) | X | X | X | X | X | X | X |
| INK MARKERS (PERMANENT) | X | X | X | X | X | X | X |
| SAMPLING JARS/BOTTLES (NON-GLASS) |  |  |  |  |  | X |  |
| COMPASS (PRIMARY EXTERIOR USE) | X | X | X | X | X | X | X |
| LABELS (GENERAL) | X | X | X | X | X | X | X |
| PHASE ZERO SCREENING RIBBONS (3/4 X 24") OR PRESSURE SENSITIVE TAPE (COLOR CODED) |  | X | X | X | X |  | X |
| EXTENSION CORD (GENERAL PURPOSE) | X | X | X | X | X | X | X |
| GENERAL PURPOSE SMALL HOUSEHOLD TOOLS | X | X | X | X | X | X | X |
| DOCUMENTATION (FORMS) (REFERENCE ATTACHED) | X | X | X | X | X | X | X |

ITEMS (OPTIONAL)

SAMPLING STAND
HEAT GUN
HEPA VACUUM CLEANER & FILTERS
CAMERA (35 MM COLOR)
DISPOSABLE CLOTHING
TAPE MEASURE/WALKER

LEGEND:

A – RADON
B – VOC's
C – PARTICULATES
D – FORMALDEHYDE
E – ASBESTOS
F – LEAD IN WATER
G – LEAD BASED PAINT (OPTIONAL)

FIG. 4D

| EQUIPMENT | LEGEND | | | | | | |
|---|---|---|---|---|---|---|---|
| | A | B | C | D | E | F | G |
| – RESPIRATOR (TYPE A) HALF OR FULL FACE/NEG. PRESSURE (OPTIONAL) | | | | | | | |
| – CARTRIDGES (HEPA) RESPIRATOR (OPTIONAL) | | | | | | | |
| – RADON CANISTER(S) | X | | | | | | |
| – DRAEGER DETECTION TUBE | | | | X | | | |
| – AIRMONITORING PUMPS | | X | X | | | | |
| – CASSETTES & TENAX TUBES (AIR MONITORING) | | X | X | | | | |
| – CALIBRATING AIR PUMP EQUIPMENT | | X | X | | | | |
| – XRF SPECTRUM ANALYZER (SCITEC) OPTIONAL | | | | | | | |
| – LEAD BASED PAINT TEST SWABS | | | | | | | X |

LEGEND:

A – RADON
B – VOC'S
C – PARTICULATES
D – FORMALDEHYDE
E – ASBESTOS
F – LEAD IN WATER
G – LEAD BASED PAINT (OPTIONAL)

SYSTEM AND PROTOCOL FOR RESIDENTIAL ENVIRONMENTAL ASSESSMENT

BACKGROUND OF THE INVENTION

Indoor contaminants in residential properties can be a significant environmental health problem. Various health affects have been linked with occupant exposure to various toxic and hazardous substances known to cause cancer in humans. Cancer is probably the most dreaded disease affecting humans, especially pregnant women and children exposed to indoor environmental health contaminants. One of four Americans, approximately two million people per year, eventually will develop cancer if trends continue. Based upon extensive studies, 80% to 90% of all cancers are caused by environmental factors, in the home or at the work place. By definition, carcinogens cause malignant tumors. An increase in malignant tumors is a sign of carcinogenicity. Cancer is a family of more than 100 different types of diseases, all characterized by uncontrolled growth and spread of abnormal cells (malignancy). Regulatory agencies simplify the matter by classifying all chemicals producing abnormal growth whether benign or malignant, as carcinogens.

A few known human carcinogens, such as asbestos, lead and vinyl chloride are regulated under Occupational Safety and Health Administration (OSHA). OSHA lists 25 carcinogenic substances. The National Toxicology Program's (NTP) Fifth Annual Report on Carcinogens lists 22 known and 140 suspected carcinogens. The higher the dose of a chemical carcinogen, the greater the number of people who will develop cancer associated with exposure to the chemical. However, indoor cancer pollutants can be eliminated or abated by performing an environmental assessment for residential properties and if the results of inspecting, testing, and assessment show signs that emissions from hazardous substances exceed established threshold levels, remediation (cleanup) should follow.

Up until now, there was no standard, specification or protocol for conducting an environmental assessment for residential properties. However, the U.S. EPA has developed guidelines for environmental assessments for commercial and industrial properties. Such environmental assessments are known as Phase I and Phase II. Phases I and II were developed primarily to protect human health and the environment as well as to satisfy the "disclosure" and "due diligence" criteria for commercial and industrial real estate transactions.

Due diligence is the exercise of "good commercial or customary practice" and is the only significant defense against liability (property damage and personal liability) for past environmental hazards for parties to real estate transactions. Federal, state and local environmental laws have been promulgated for "commercial and industrial" properties which require an Environmental Assessment of the property, Phase I and Phase II, in order to satisfy the "due diligence" criteria.

A Phase I Environmental Assessment includes a visual site inspection of the property in order to make the client aware of reasonable suspicions of environmental conditions that may have an adverse environmental impact on the property and its occupants. Phase I does not include sampling and collecting hazardous substances or laboratory testing. If the client desires, a Phase II follows which generally includes sampling, collecting, laboratory testing/analysis, assessment and response action (remediation) recommendations(s). A Phase III includes the scope of work, design, plan and specification for remediation and dictates the contractual terms and conditions required for the cleanup work.

The performing of a Phase I and II Environmental Assessment for residential properties using the U.S. EPA guidelines established for commercial and industrial properties is cost prohibitive, especially since Phase I alone (without sampling, collecting and testing) would have little value for a residential property, and Phase II would necessarily follow. There is, therefore, a critical need to develop an affordable Environmental Assessment for residential properties and at the same time, satisfy the most important "due diligence" criteria.

As a result, this invention of a cost effective, comprehensive environmental system and protocol, termed the Phase Zero Environmental Assessment, has been designed.

The Phase Zero Environmental Assessment is a low cost comprehensive inspection, detection, sampling, testing, and assessment standard for residential properties that follows the guideline established by the U.S. EPA for Phase I and Phase II for commercial and industrial properties including satisfying the "disclosure" and "due diligence" criteria.

The Phase Zero system and protocol addresses presently known relevant indoor toxic and hazardous cancer causing substances such as asbestos, radon, lead in water, particulates, volatile organic compounds, formaldehyde and lead based paint. Testing for other contaminants if any, are optional and available to the property owner at additional cost.

Upon the completion of Phase Zero Environmental Assessment a "Certificate of Environmental Compliance" is issued to the property owner showing the property met the environmental emission standards established by the U.S. EPA or other government environmental agencies. In the event the inspection and assessment show one or more hazardous substances to be above the acceptable standards, a response action (cleanup) is recommended to remedy the hazard, and if requested, several independent third party qualified cleanup contractors are referred. The environmental inspectors are also available to perform final clearance (sampling, air monitoring and testing) and recertification for environmental compliance once the hazard(s) have been abated by the contractor.

The Phase Zero system and protocol may be used for all residential properties, single and multi-unit family homes, apartments, condominiums, cooperatives, retail shops, strip shopping stores, etc.

There is a great potential for major public health benefits to be realized by widespread consumer use of the Phase Zero Environmental Assessment system and protocol for residential properties. If the Phase Zero Environmental Assessment shows that one or more hazardous substances measure above established recommended emission standards, a response action for property remediation would necessarily follow which would eliminate or reduce the indoor toxic and/or cancer causing substances at an affordable cost, without any increased risk to consumers.

Consequently, the improvement in public health results to be realized by routine, widespread use of the Phase Zero system and protocol will be immediate and measured in the avoidance of thousands of deaths and hundreds of thousands of persons hospitalized annually.

Also, utilization of the Phase Zero Environmental Assessment would meet the "innocent land owner defense" criteria since inspection, detection, sampling, testing and assessment of the real property conducted by environmental professionals, to determine or discover the obviousness of the presence or likely presence of a release of toxic or hazardous substances on the property and a review of other sources of information concerning previous ownership and use would satisfy the "disclosure" and "due diligence" criteria as a defense against liability for remediation (cleanup) costs for past environmental health hazards for parties to current real estate transactions.

The utilization of the Phase Zero Protocol would, therefore, protect all parties in the real estate transaction including the real estate broker, the seller and the lending institute (mortgage) against:

STATUTORY LIABILITY: Breach of any statutory duty to disclose material facts regarding the condition of the property.

NEGLIGENCE: Negligently failing to disclose material facts regarding condition of the property and intentionally not representing the condition of the property.

MISREPRESENTATION/FRAUD: Intentionally failing to disclose material facts regarding condition of the property and intentionally misrepresenting the conditions of the property.

The Phase Zero system and protocol is designed to benefit the consumers and buyer of residential properties from indoor environmental health hazards and to protect all the parties in the real estate transaction against potential liability arising from misrepresentation, fraud, negligence or non-disclosure of the environmental condition of the property. At the present time, there are no known systems for assessing environmental contaminants in residential properties that have established standards, guidelines or protocols, except for the system of this invention.

OBJECTS OF THE INVENTION

It is the general object of this invention to provide a system and protocol for environmental assessment which overcomes the shortcomings of piece-meal techniques, without any established standards, for residential properties, in present use.

It is another object of this invention to provide a system and protocol for environmental assessment which costs less than existing systems and protocols.

It is yet another object of this invention to provide a system and protocol for environmental assessment which protects the parties in real estate transactions against allegations of statutory liability.

It is still yet another object of this invention to provide a system and protocol for environmental assessment which protects the parties in real estate transactions against accusations of negligence.

It is an additional object of this invention to provide a system and protocol for environmental assessment which protects the parties in real estate transactions against accusations of misrepresentation or fraud.

It is yet an additional object of this invention to provide a system and protocol for environmental assessment which protects the buyers of real estate property from unanticipated costs in the removal of environmental hazards.

It is still yet an additional object of this invention to provide a system and protocol for environmental assessment which uses standardized equipment, materials, and forms, in conducting the assessment.

It is an added object of this invention to provide a system and protocol for environmental assessment which protects the occupants of residential properties from environmental health hazards.

It is yet an added object of this invention to provide a system and protocol for environmental assessment which follows the guidelines established by the United States Environmental Protection Agency for commercial and industrial properties.

SUMMARY OF THE INVENTION

These and other objects of this invention are achieved by providing to the person making the environmental assessment a standardized test kit of preselected materials, a standardized set of forms for recording the results of the inspection and assessment, and a methodology or protocol for carrying out the assessment.

The assessment comprises an initial survey of the inside of the building to determine potential sources of hazardous materials. The most common type of hazardous materials are included in the survey. During this initial inspection, the potential sources of hazardous materials are tagged using tapes or ribbons. These are color coded to identify the category or type of hazardous materials.

At least one sample of several types of the potentially hazardous materials, such as asbestos, particulates, lead in water, radon and volatile organic compounds, is collected and placed in respective containers which are included in the test kit, for later evaluation by a testing laboratory. Levels of other types of contaminates, such as formaldehyde, and lead in paint can be read directly on site using metering devices. After the inspection, sampling, testing and documentation of the inside of the structure is completed, a similar survey is made of the exterior and neighboring areas of the structure.

After the interior and exterior inspection is completed, the laboratory results are reviewed and analyzed, and the report is sent to the interested party, either certifying that the property meets the required hazardous material limits or describing the areas in which these limits are not met.

DESCRIPTION OF THE DRAWING

Other objects and many of the intended advantages of this invention will be readily appreciated as the same becomes better understood by reference to the following description when considered in connection with the accompanying drawing wherein:

FIGS. 3A and 3B show the inspection checklist used by the inspector in performing the environmental assessment of the inside of the building;

FIG. 3C shows the environmental assessment property description; and

FIGS. 3D shows the inspection checklist for the exterior of the building.

FIG. 4A shows a listing of the various types of suspected contaminants which are assessed, the number of samples required and the test method.

FIG. 4B(1-2) shows a listing of the toxic and hazardous material with their sources, their sampling and testing method, their probable location and the remediation methods.

FIG. 4C shows a listing of the items in the tool kit provided to the inspector and where they are used.

FIG. 4D shows a listing of equipment made available to the inspector for the environmental assessment.

DETAILED DESCRIPTION OF THE PREFERRED EMBODIMENTS

Figure 1:
FIG. 1 is a photograph showing the contents of the test kit.

To achieve an affordable cost for the system and protocol for environmental assessment, and at the same time, support the requirement for protecting human health and the environment, and satisfy the disclosure and due diligence criteria for the real estate transaction, the following methodology and design parameters were utilized and implemented in developing the system and protocol.

PARAMETERS (STANDARDS SET)

1. Commonality of tools, materials, supplies and documents (forms) coupled with the development of the "Phase Zero Screening/Test Kit" for use in screening, (identifying) sampling, collecting and testing the various assumed and suspect hazardous materials.

2. Interrelationship of the tools, materials, supplies and documents (forms) used for the various toxic and hazardous substance identified, sampled, collected and tested.

3. The establishment of a precise sequence of events and time and motion, investigation and detection of each and every room, hallway, space and homogenous area of the property and the subsequent tagging (Phase Zero Screening Ribbons) of all assumed or suspect Phase Zero hazardous materials. The screening ribbons are color-coded and allow the inspector to work through the property and visually detect the presence of hazardous material, tag same and not interrupt the survey by stopping to take or collect samples for delivery to the testing laboratory. Only after the complete walk through and tagging process does the inspector start the sampling and collecting procedures. The inspector returns to the color-coded ribbons, and records the material type/location, etc., and samples and collects only the critical, most sensitive areas in accordance to the number of tests prescribed by the Phase Zero Protocol.

4. Limiting the number of sampling and laboratory tests in the Phase Zero Protocol per suspect hazardous material detected, but maintaining the integrity and quality assurance of the Environmental Assessment by locating and color coding assumed and suspect hazardous material throughout the property as follows:

Each hazardous material being investigated with the exception of radon and lead in water, is identified and located throughout the property by the inspector tagging each area location with the various color-coded screening ribbons. After all the assumed and suspect hazardous materials are screened and tagged with color-coded ribbons, the inspector visually reinvestigates only one hazardous material at a time. He then selects the most critical area or areas for sampling, collecting and testing (based upon the limits specified in the protocol) and records the information on the sample container and the sampling data sheet. The inspector then records on his data sheet one or more tagged area sample locations that were not selected for testing.

5. The Phase Zero affordable cost was also made possible by using only one regional or one national accredited independent testing laboratory by all Phase Zero environmental inspectors regardless of where they are located. This results in a considerable dollar volume discount and other cost reductions due to standardization of forms for use by the testing laboratory selected.

FIG. 4A gives a listing of the toxic and hazardous materials that are tested with the number of samples required and the types of tests made.

FIG. 4B is a reference guide for inspectors with regard to the sources, sampling methods, probable location and remediation (cleanup) of the seven major types of toxic and hazardous materials covered in this system.

A standardized test kit is used by the inspector in making the environmental assessment. FIG. 1 shows the items included in the test kit.

The environmental home inspector carries and transports to the property site, a kit or container holding all the necessary tools, materials, supplies and documents necessary for the screening, sampling and collection of all Phase Zero assumed or suspect hazardous materials for laboratory delivery and analysis to a designated accredited testing laboratory. Due to inter-relationships of the Phase Zero hazardous substances investigated, there is a commonality of items used in the screening, sampling and collection procedure. Therefore, similar tools, materials and supplies are color-coded for screening, quick identification and efficiency in conducting the inspection, detection, sampling and collection. The color-coded legend covering the Phase Zero Protocol follows:

ASBESTOS - Red
PARTICULATES - White
VOLATILE ORGANIC CHEMICALS - Yellow
FORMALDEHYDE - Green
LEAD BASED PAINT (Optional) - Blue No color-codes are necessary for lead in water and radon.

Tools, materials and supplies for sampling and collecting asbestos containing building material and lead based paint (optional) are similar as well as other hazardous material investigated, including the collecting and sampling of particulates and volatile organic compounds.

The Phase Zero test kit -also contains color-coded "screening ribbons" (tags) which are Used to loeate and identify all Phase Zero assumed or suspect indoor hazardous materials located throughout the property as visually identified by the environmental home inspector. These tags are called the "Phase Zero Screening Ribbons", which are attached to assumed or suspect hazardous surfaces by means of string(s), pin(s) or glue, depending on the type and shape of the attaching surface being investigated. It should be noted that after the walk through and tagging completion, the inspector shall decide which tags represent the most critical areas to be sampled and collected since the Phase Zero Protocol's pricing structure was established as an affordable design criteria and the number of laboratory tests are limited. Additional laboratory tests may be recommended by the inspector to revalidate an assessment which would represent an added cost to the property owner.

The Phase Zero Test Kit and the Phase Zero Screening Ribbons were designed to decrease the time of the inspection, increase the overall efficiency and reduce the cost to an affordable Environmental Assessment for residential property owners.

The test kit items and their usage are shown in FIG. 4C.

In addition to a standardized test kit, the inspector is given a standard list of equipment to conduct the assessment. The equipment listing and their usage is shown in FIG. 4D.

The specifications for the air monitoring equipment is given below.

EQUIPMENT SPECIFICATION(S) PARTICULATES HIGH VOLUME SAMPLER #A100 (MFG. BY ALLEGRO)

The high volume sampler is designed to offer a variable flow setting 3 to 20 liters with a filter cassette in line. The sampler comes complete with a separate cassette stand, variable flow regulator and 5 feet of PVC tubing. The regulator features a lock-in capability which prevents pump vibrations or personnel tampering from readjusting the flow setting. The A100D includes an hour meter and AHERA timing record.

| SPECIFICATIONS | |
| --- | --- |
| PUMPS - | Rotary, oil less, carbon vane 1/10th H.P. includes in line filters and muffler, feet handle and power cord with switch. |
| REGULATOR - | ⅜" needle valve with lock-in flow feature sampling range (3-20 LPM). |
| STAND - | Adjustable aluminum tripod (1-5 feet). |
| TUBING - | System includes 5 feet of clear tubing ready to attach sample cassette.k |
| SYSTEM WEIGHT - | 9.5 pounds. |
| MAXIMUM FLOW RATE - | 20 LPM w/37 mm cassette. |

A standardized set of documents (inspection forms) are used by the inspector.

Figure 2A:
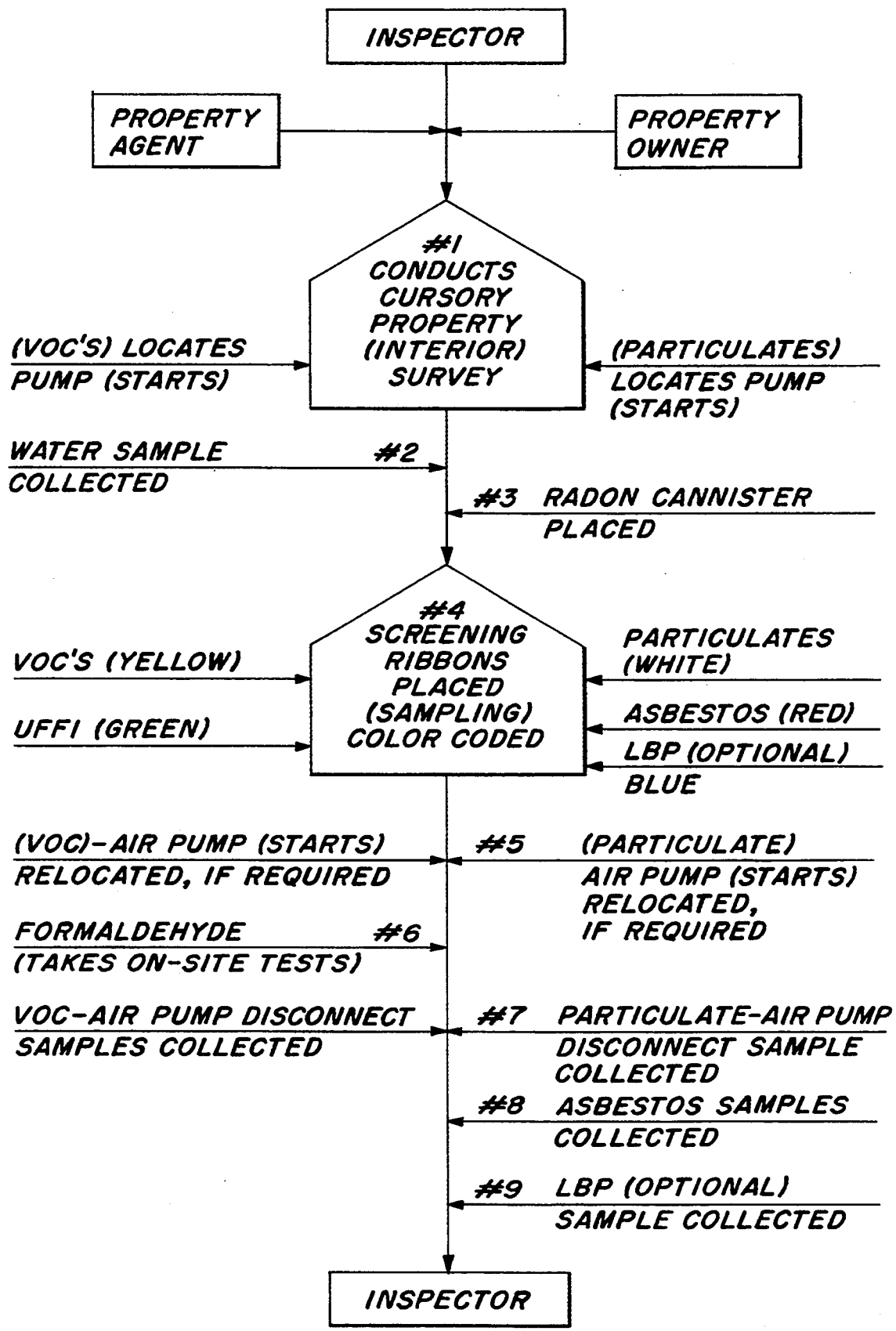
FIGS. 2A and 2B are a flow chart diagram which illustrates the steps taken by the inspector who is performing the environmental assessment.
Figure 2B:
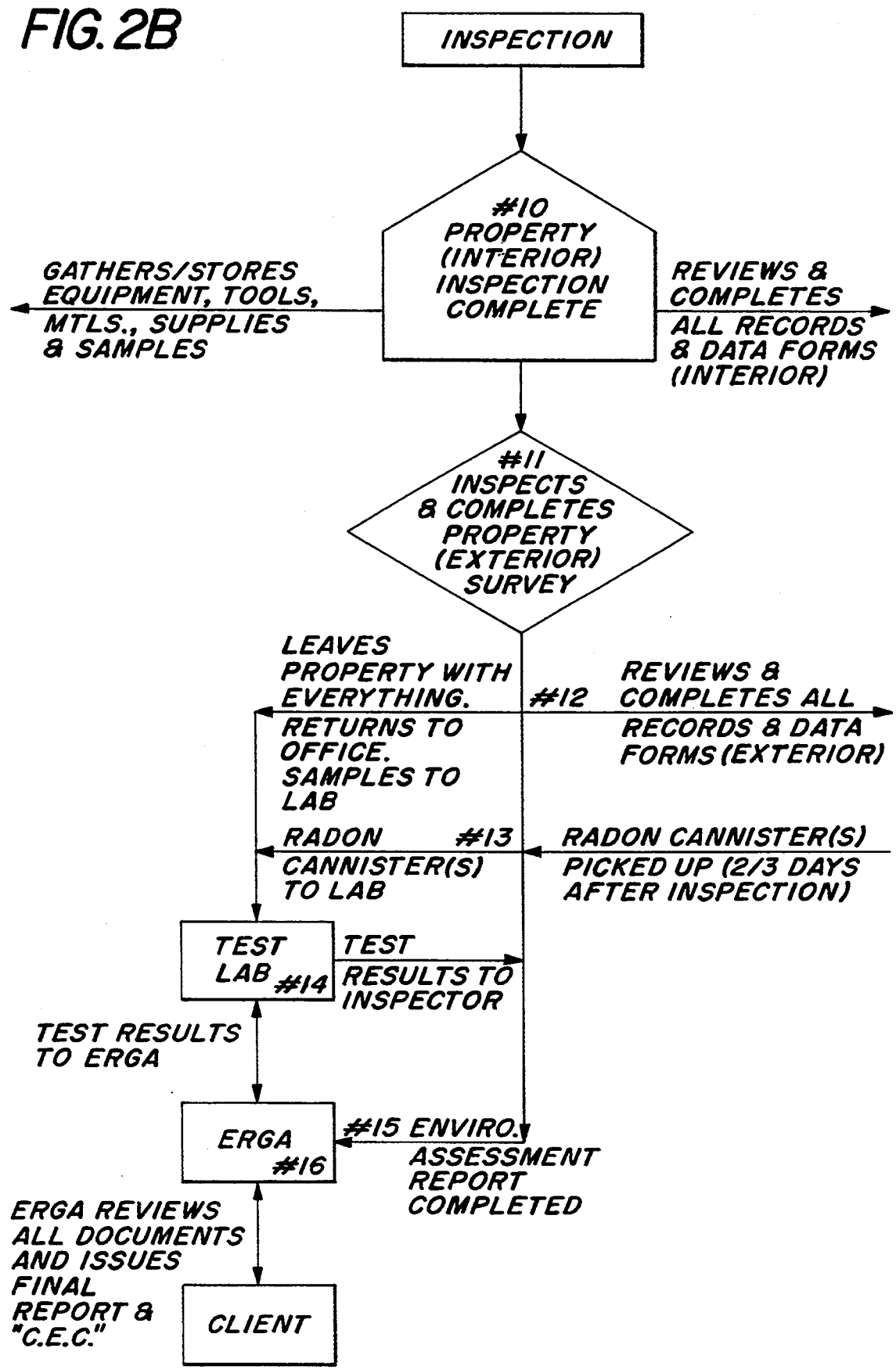

FIGS. 2A and 2B show, in flow diagram form, the step-by-step procedure used by the inspector for environmentally assessing a property. In FIGS. 2A and 2B, and in the description below, the term ERGA refers to the Environmental Realty Guild Corporation of America, Inc., the assignee of this patent application and the operator of the system and protocol. The Environmental Inspector enters the property to be environmentally assessed utilizing Phase Zero system and protocol. The inspector carries his inspection manual, including standard specifications and procedures, documents and data forms, the Phase Zero Test Kit (including the Phase Zero screening ribbons) and any on-site testing equipment required for the inspection (air pumps, Draeger Detection Tube, etc.)

The inspection proceeds step by step in the following sequence, after the inspector meets with the property owner.

STEP #1 The inspector performs a cursory survey of the entire interior of the property and as a result immediately identifies the best location(s) for the low and high volume air pumps and starts up the pumps to sample for Volatile Organic Compounds and Particulates.

STEP #2 The inspector locates the largest source of water consumed on the property (away from the incoming water source), usually the kitchen faucet and collects a sample of water.

STEP #3 The inspector immediately proceeds to the basement area or lowest livable level of the property and places the Radon Canister (E-PERM).

STEP #4 Starting from the basement, the inspector proceeds to survey the entire interior of the property by traversing from basement, crawl space room to room, floor to floor, attic, etc., and proceeds to tag (color-coded) Phase Zero Screening Ribbons on assumed or suspect toxic and hazardous material covered in the Phase Zero Protocol, including the previously located rooms (areas), the air pumps are placed. The screening ribbons are placed by the inspector to locate and identify Volatile Organic Compounds, Particulates, Formaldehyde, Asbestos and Lead Based Paint, (optional).

STEP #5 After the inspector tags (color-coded screening ribbons) the area location for all assumed and suspect hazardous material investigated in Step 4, he returns to the area locations previously selected for air sampling (pumps) of the VOC's and Particulates. In the event the inspector identifies by visual reinvestigation that another tagged are is more critical than where the air pumps were initially located, he disconnects the pumps, aborts the prior air sampling and relocates the air pumps to the more critically designated area.

For Particulate air sampling, a high volume air sampler (pump) operates for about an hour at a flow rate from 15 to 17 liters per minute.

For VOC's a low volume air sampler (pump) operates for about thirty minutes at a flow rate of 50 liters per minute.

The sampling, collecting and recording for VOC's and Particulates in accordance to Appendix B and C.

Only one VOC and one Particulate sample is collected and recorded for testing with ERGA's designated accredited laboratory and based upon the discretion of the inspector at least one or more of each of the most critical areas tagged for sampling, but not collected, is recorded (located) on the sampling data sheet.

STEP #6 The inspector then visually identifies and selects the most critical area location tagged (color-coded screening ribbons) for Formaldehyde and manually operates the on-site DRAEGER detection tube instrument (disposable cassettes). He takes one reading and records the results on the sampling data sheet. The inspector has the discretion to take one or more additional on-site readings if he suspects other tagged area locations to be critical.

STEP #7 During the performance of Step #6 and/or #8, and as time allows, the inspector returns to the low and high volume air pumps set up to sample the VOC's and Particulates and disconnects the power source of the pumps at the end of the designated operational time allowed for sampling. The inspector removes (collects) the cassette(s) and or Tenax Tubs and records the necessary information. Reference to Step #5. The cassette(s) and/or Tenax Tubes are placed in the Phase Zero Screening/Test Kit for future laboratory testing. Reference to Step #5.

STEP #8 The inspector then visually identifies and selects three to five of the most critical (friable) area locations tagged (color-coded screening ribbons) for assumed or suspect asbestos containing building materials. All three to five of the most critical area locations tagged and selected are sampled, collected and recorded but only two of the most critical samples are delivered to ERGA's designated accredited laboratory for analysis. The remaining samples collected are stored for future testing as necessary.

STEP #9 (option) If a lead based paint Phase Zero (option) Environmental Assessment is authorized by the property owner, one of two methods of inspection, detection, sampling, collecting and testing is utilized.

Method #1 (Lead Based Paint Chemical Test Swab) The inspector visually identifies and selects all critical (chipped, damaged, deteriorated) area locations, tags same (color-coded screening ribbons) for assumed or suspect Lead Based Paint. Test swabs are then rubbed over each (prepared) exposed bare surface tagged. The inspector notes any color change which indicates Lead Based Paint. However, for negative results (no or little color change) the inspector shall collect two bulk samples (about 2 square inches of paint film) for verification testing and analysis by ERGA's accredited laboratory.

Method #2 (XRF Spectrum Analyzer, Scitec Device) The sampling and testing of Lead Based Paint by using a XRF Spectrum Analyzer Scitec Device is presently cost prohibitive for residential properties. However, if any X-Ray Fluorescence test is requested by the property owner, and he is willing to bear the added cost, the inspector shall follow HUD Lead Based Paint Interim Guide Lines for hazardous identification and abatement in public and Indian housing.

STEP #10 The property (interior) environmental assessment is now complete and the inspector gathers all his equipment, tools, materials, supplies, test samples and documents and places them in a secure area of the property or carries and stores them in his vehicle. Prior to storage, the inspector reviews and completes all records and data forms.

STEP #11 The inspector next completes the property (exterior) environmental assessment by walking around and about the outside of the property (exterior) and conducts a visual inspection of all outside assumed or suspect toxic and hazardous substances. He then fills out the Phase Zero Inspection Checklist developed by ERGA for property (exterior).

STEP #12 The inspector reviews and completes all documents and data forms (both property interior and exterior). He then leaves the property, returns to his office and mails or delivers the collected samples to ERGA's designated accredited testing laboratory.

STEP #13 Within 48 hours to 72 hours after the inspection is completed, the inspector or his certified Radon Technician picks up the canister(s) placed in the property. He records the canister(s) number(s), the floor level, location and common name of the room in the space provided to the right of each canister. (Reference Step #3). The inspector then mails or delivers the canister(s) to the designated ERGA testing laboratory for analysis.

STEP #14 The designated accredited testing laboratory simultaneously returns a copy of all test results to the inspector.

STEP #15 Based upon the lab test results, the inspector completes his inspection report, including all ERGA data forms and the lab report and mails or delivers all of the documents to ERGA's representative.

STEP #16 ERGA's representative reviews the final inspection documents received from the inspector and completes ERGA's Certificate of Environmental Compliance Form. ERGA's representative mails or delivers the "Certificate of Environmental Compliance" to the property owner or agent with other pertinent environmental documentation, such as recommended remedial work (cleanup), referral of abatement contractors or suggested additional testing.

FIGS. 3A and 3B show the phase zero inspection checklist for the inspector. In addition to listing the information concerning the property, the inspector, in filling out the checklist, is required to give information as to the location in which the sampling was taken, the sampling time, the sampling conditions, and other important information regarding the inspection and sampling procedure. Included, in addition, is the information regarding the inspection of the exterior of the building. As can be seen in the inspection checklist, the contaminants assessed and sampled include asbestos, radon, particulates in air, volatile organic compounds, urea formaldehyde gas, lead-based paint, and municipal drinking water. Also included on the checklist is information regarding the visual inspection of the interior of the building as well as the visual inspection of the exterior of the building.

FIG. 3D shows the inspection checklist for the exterior of the property. The items that are specifically checked include the suspicion of radon on the property or a neighboring property, any waste sites on the property or a neighboring property, any visible storage tanks or underground tanks with visible vents or fill pipes, soil or ground contamination, and whether the neighboring property has gas stations, manufacturing plants, storage or delivery of oil or gas, or other facilities. Also included is information regarding the presence of aboveground storage tanks and septic tanks, as well as information on the property that is being inspected.

A system and protocol for environmental assessment has been described which uses standard tools, equipment and forms to provide a low-cost assessment for residential and similar properties, including singular and multi-unit family homes, apartments, condominiums, cooperatives, retail shops, strip shopping stores, and the like. It protects all of the parties included in real estate transactions such as the broker, the lending agency, the buyer and the seller, and performs the assessment is in accordance with the United States Environmental Protection Agency guidelines presently used for the environmental assessment of commercial and industrial properties. The standardized protocol, tools, documentation and equipment enables the environmental assessment to be performed faster and at a much lower cost than the uncoordinated and piecemeal environmental assessments presently being performed for residential properties.

Without further elaboration, the foregoing will so fully illustrate my invention that others may, by applying current or future knowledge, readily adapt the same for use under the various conditions of service.

I claim:

1. A method for the environmental assessment of a static structure comprising the steps of:
   (a) assembling and providing a kit of predetermined tools, materials, and documentation, said documentation comprising forms which define a protocol of step-by-step procedures for testing the levels of respective ones of a plurality of predetermined contaminants, said materials comprising securable tapes and ribbons which are color coded to identify the respective predetermined contaminants;
   (b) providing selected, standard, commercially available, off-the-shelf, testing equipment;
   (c) inspecting interior locations within said structure for the predetermined contaminants;

(d) determining if any of the predetermined contaminants is suspected to be within the structure and the suspected location thereof;
(e) recording said suspected contaminants and the locations thereof on said forms;
(f) tagging each of said suspected locations with a selected one of said securable tapes and ribbons to indicate the type of suspected contaminant to be thereat;
(g) taking samples of a selected number of said suspected contaminants from said suspected locations;
(h) packaging each of said samples; and
(i) shipping said samples to a testing laboratory.

2. The method of claim 1 wherein said tools and materials comprise a flashlight, a drop cloth, a core borer, a knife, an adhesive, a spray sealant, a spray container, a duct tape, paper towels, and a sampling jar with labels and a marker pen.

3. The method of claim 2 wherein said forms comprise checklists for said environmental assessment.

4. The method of claim 1 wherein said step of taking samples comprises sampling drinking water, asbestos, volatile organic compounds, particulates in air, radon gas, and formaldehyde (UFFI).

5. The method of claim 4 wherein said step of taking samples further includes sampling of lead-based paint.

6. The method of claim 5 wherein the step of taking samples further comprises removal of samples of lead-based paint using a knife provided in said kit, and placing said samples in a container provided in said kit.

7. The method of claim 4 wherein said taking of samples further comprises determining the levels of lead in said lead-based paint using an XRF Spectrum Analyzer.

8. The method of claim 4 wherein the step of taking samples of said drinking water further comprises collecting said drinking water in a sterile jar provided in said kit.

9. The method of claim 4 wherein said step of taking samples further comprises sampling the levels of said formaldehyde using a Draeger Detection Tube.

10. The method of claim 4 wherein said step of taking samples further comprises removal of samples of asbestos material, using said tools provided in said kit, and placing said asbestos samples in a container provided in said kit.

11. The method of claim 4 wherein said step of taking samples further comprises the step of sampling the levels of volatile organic compounds using an air sampling pump and placing the samples collected into a container provided in said kit.

12. The method of claim 4 wherein said step of taking samples further comprises sampling of particulates in air using an air pump to collect samples and placing said samples in a container provided in said kit.

13. The method of claim 4 wherein said step of taking samples of said radon gas comprises the step of collecting said samples in a charcoal canister and placing said canister in a container provided in said kit.

14. The method of claim 4 wherein said step of taking samples further includes sampling of lead-based paint.

15. The method of claim 14 wherein the step of taking samples further comprises removing samples of lead-based paint using a knife provided in said kit, and placing said samples in a container provided in said kit.

16. The method of claim 14 wherein said taking of samples further comprises determining the levels of lead in said lead-based paint using an XRF Spectrum Analyzer.

17. The method of claim 4 wherein the step of taking samples of said drinking water further comprises collecting said drinking water in a sterile jar provided in said kit.

18. The method of claim 4 wherein said step of taking samples further comprises determining the levels of said formaldehyde using a Draeger Detection Tube.

19. The method of claim 4 wherein said step of taking samples further comprises removal of samples of asbestos material, using a knife provided in said kit, and placing said asbestos samples in a container provided in said kit.

20. The method of claim 4 wherein said step of taking samples further comprises the step of sampling the levels volatile organic compounds using an air sampling pump and placing the samples collected into a container provided in said kit, 21. The method of claim 4 wherein said step of taking samples further comprises sampling of particulates in air using an air pump to collect samples and placing said samples in a container provided in said kit.

22. The method of claim 4 wherein said step of taking samples of said radon gas comprises the step of collecting said samples in a charcoal canister and placing said canister in a container provided in said kit.

23. The method of claim 4 wherein said method further comprises the steps of receiving and evaluating the report of said testing laboratory.

24. The method of claim 23 wherein said method further comprises the step of generating a report on the results of said environmental assessment of said property.

25. The method of claim 4 wherein said method further comprises the steps of inspecting the exterior area of said structure and determining the presence and location of suspected contaminants in said exterior area and the areas adjacent said exterior area.

26. A system for the environmental inspection and assessment of the interior and exterior of a building, including the surrounding area, by an inspector, said system comprising:
(a) forms defining a protocol of step-by-step procedures for conducting said environmental inspection and for the assessment of the levels of a plurality of predetermined contaminants by the inspector;
(b) a preselected kit of tools, materials and equipment comprising a measuring tape and a compass for determining and recording the location of said contaminants, and a ladder, a flashlight, a drop cloth, sampling containers, a borer and a knife, a caulking gun and caulk, space sealing duct tape, paper towels, a vacuum cleaner, ink markers and labels, said kit of tools, materials and equipment being used in combination with said forms by the inspector for inspecting and assessing the plurality of the predetermined contaminants within the interior of the building in accordance with said protocol as defined by said forms.

27. The system of claim 26 wherein said forms comprise inspection checklists for recording the presence and location of said contaminants.

28. The system of claim 27 wherein said kit of tools, materials and equipment comprises securable tapes and ribbons for marking the locations within said building of suspected ones of said contaminants.

* * * * *